US012779509B2

(12) United States Patent
Takikawa

(10) Patent No.: US 12,779,509 B2
(45) Date of Patent: Nov. 3, 2026

(54) CLEANING TOOL FOR SURGICAL INSTRUMENT

(71) Applicant: RIVERFIELD INC., Tokyo (JP)

(72) Inventor: Kyohei Takikawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 124 days.

(21) Appl. No.: 18/988,060

(22) Filed: Dec. 19, 2024

(65) Prior Publication Data

US 2025/0114827 A1 Apr. 10, 2025

Related U.S. Application Data

(63) Continuation of application No. PCT/JP2022/026375, filed on Jun. 30, 2022.

(51) Int. Cl.
*B08B 3/08* (2006.01)
*A61B 90/70* (2016.01)

(52) U.S. Cl.
CPC ................ *B08B 3/08* (2013.01); *A61B 90/70* (2016.02)

(58) Field of Classification Search
None
See application file for complete search history.

(56) References Cited

U.S. PATENT DOCUMENTS

| | | | | |
|---|---|---|---|---|
| 10,350,318 | B2 * | 7/2019 | Sharma .................. | A61B 1/123 |
| 10,588,706 | B2 * | 3/2020 | Limon ................... | A61B 34/35 |
| 2015/0027502 | A1 | 1/2015 | Yamamoto et al. | |
| 2016/0242868 | A1 | 8/2016 | Robert et al. | |

FOREIGN PATENT DOCUMENTS

| | | | |
|---|---|---|---|
| JP | 2013-188387 | A | 9/2013 |
| JP | 2016-073907 | A | 5/2016 |

* cited by examiner

*Primary Examiner* — Rita P Adhlakha
(74) *Attorney, Agent, or Firm* — Sughrue Mion, PLLC

(57) ABSTRACT

A cleaning tool for a surgical instrument that includes a housing includes a first holder, a second holder, and a coupling part. The first holder holds a first connector that is insertable into the housing to discharge a cleaning solution in a first discharging direction that is parallel to a direction in which the first connector is inserted into the housing. The second holder holds a second connector that is insertable into the housing, at a position different from a position in the housing at which the first connector is inserted, to discharge the cleaning solution in a second discharging direction that is to a direction in which the second connector is inserted into the housing. The coupling part couples the first holder and the second holder so that the first discharging direction intersects the second discharging direction.

19 Claims, 12 Drawing Sheets

CLEANING TOOL FOR SURGICAL INSTRUMENT

CROSS REFERENCE TO RELATED APPLICATION

This application is a continuation application of International Patent Application No. PCT/JP2022/026375 filed on Jun. 30, 2022, the contents of which being incorporated by reference herein in its entirety.

BACKGROUND

The present disclosure relates to a cleaning tool to be used in cleaning an inside of a housing of a surgical Instrument.

There has been known a surgery assistance robot to assist surgery. Attachments are mounted on the surgery assistance robot in accordance with the purpose of the surgery. The attachments are also called instruments, and specifically, are medical devices. The instruments can include forceps and electric scalpels.

Furthermore, the instruments can include reusable devices. In the case of reusable instruments, the reusable instruments are cleaned after use in surgery and sterilized for reuse. In some cases, for example, the reusable instruments may be repeatedly used for about ten times.

In general, three cleaning methods of ultrasonic cleaning, reduced-pressure boil cleaning, and washer disinfector cleaning (hereinafter, also referred to as "WD cleaning") have been used as methods of cleaning the medical devices. The WD cleaning involves less man-hours of work compared with the ultrasonic cleaning and the reduced-pressure boil cleaning methods, and a medical staff who performs cleaning bears less burden with WD cleaning. Thus, the WD cleaning has been implemented as a cleaning method of medical devices in a large number of facilities.

The WD cleaning is a cleaning method that combines a chemical cleaning effect obtained by detergent and a physical cleaning effect obtained by a high-pressure water flow. The WD cleaning employs a device to supply a cleaning solution at a high pressure. The WD cleaning can be also performed on the reusable instruments by using a device compatible with the instruments.

SUMMARY

It is an aspect to provide a cleaning tool that achieves stable cleaning while facilitating connection, removal, and the like of the cleaning tool.

According to an aspect of one or more embodiments, there is provided a cleaning tool for a surgical instrument that includes a housing, the cleaning tool comprising a first holder configured to hold a first connector, the first connector being configured to be inserted into the housing to discharge a cleaning solution in a first discharging direction for cleaning an inside of the housing, and the first discharging direction being parallel to a direction in which the first connector is inserted into the housing; a second holder configured to hold a second connector, the second connector being configured to be inserted into the housing, at a position different from a position in the housing at which the first connector is inserted, to discharge the cleaning solution in a second discharging direction, and the second discharging direction being parallel to a direction in which the second connector is inserted into the housing; and a coupling part coupling the first holder and the second holder so that the first discharging direction intersects the second discharging direction.

According to another aspect of one or more embodiments, there is provided a cleaning tool for a surgical instrument that includes a housing, the cleaning tool comprising a first connector arranged at an end of a first tube configured to supply a cleaning solution for cleaning an inside of the housing, the first connector being configured to be inserted into a first port provided in the housing to discharge the cleaning solution in a first discharging direction parallel to a direction in which the first connector is inserted into the first port; a first holder holding the first connector; a second connector arranged at an end of a second tube configured to supply the cleaning solution, the second connector being configured to be inserted into a second port provided in the housing to discharge the cleaning solution in a second discharging direction parallel to a direction in which the second connector is inserted into the second port; a second holder holding the second connector; and a coupling part coupling the first holder and the second holder so that the first discharging direction intersects the second discharging direction.

According to yet another aspect of one or more embodiments, there is provided a cleaning tool comprising a first holder configured to engage a groove of a first connector at a distal end of a first tube, the first connector being removably received into a first port in a housing of a surgical instrument and being configured discharge a cleaning solution into the housing in a first discharging direction parallel to a direction in which the first connector is received into the first port; a second holder configured to engage a groove of a second connector at a distal end of a second tube, the second connector being removably received into a second port in the housing and being configured to discharge the cleaning solution into the housing in a second discharging direction that is parallel to a direction in which the second connector is received into the second port and that intersects the first discharging direction; and a coupling rod coupling the first holder and the second holder.

BRIEF DESCRIPTION OF THE DRAWINGS

The above and other aspects of the present disclosure will become more clear from the following disclosure in conjunction with the drawings, in which.

DETAILED DESCRIPTION

Figure 1:
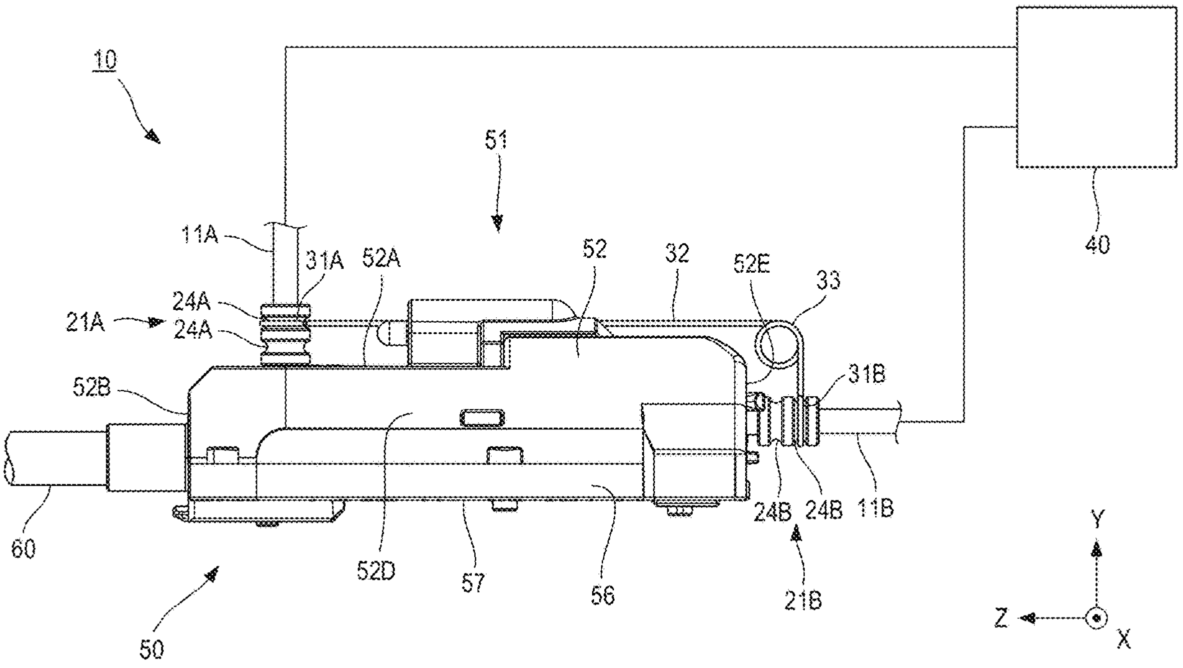
FIG. 1 is a front view explaining configurations of a cleaning tool and a surgical instrument, according to some embodiments.

In the case of cleaning an instrument by the WD cleaning, a main device for the WD cleaning injects a cleaning solution at a high pressure into the instrument. Consequently, an inside of the instrument is cleaned. The cleaning solution is a liquid containing the aforementioned detergent. The inside of the instrument after use in surgery is contaminated with a body fluid such as blood. The body fluid is washed off by the cleaning solution injected from the main device into the instrument.

As a configuration of supplying the cleaning solution to the instrument at a high pressure, for example, a configuration to supply the cleaning solution from the main device for the WD cleaning to the instrument via a cleaning tube may be used. In this configuration, an end of the cleaning tube adjacent to the instrument is provided with a connector. Moreover, the instrument is provided with a cleaning port corresponding to the cleaning connector. The cleaning connector of the cleaning tube is inserted into and connected to the cleaning port. Accordingly, the cleaning solution is supplied into the instrument at a high pressure from the main device for the WD cleaning.

In order to reduce the burden of the medical staff who perform the cleaning, it is advantageous that the configuration facilitates connection and removal between the cleaning connector and the cleaning port. It is advantageous that the configuration enables the cleaning connector to be connected to the cleaning port by inserting the cleaning connector into the cleaning port, without performing an additional operation of, for example, rotating the cleaning connector and the cleaning port relative to each other. Similarly, it is advantageous that the configuration enables the cleaning connector to be pulled out and removed from the cleaning port by separating the cleaning port and the cleaning connector from each other without performing an additional operation of, for example, rotating the cleaning connector and the cleaning port relative to each other.

However, if the cleaning solution is injected at a high pressure in the case of adopting the configuration of facilitating the connection and the removal, there may be an increasing possibility that the cleaning connector is removed from the cleaning port in reaction to the injection. If the cleaning connector is removed unintentionally, there may be an occurrence of a cleaning failure.

Various embodiments described herein provide a cleaning tool that achieves stable cleaning while facilitating connection, removal, and the like of the cleaning tool.

According to an aspect of one or more embodiments, a cleaning tool is a cleaning tool for a surgical instrument that includes a housing. The cleaning tool includes: a first holder configured to hold a first connector, the first connector being configured to be inserted into the housing to discharge a cleaning solution for cleaning an inside of the housing, and configured to discharge the cleaning solution in a first direction in which the first connector is inserted into the housing; a second holder configured to hold a second connector, the second connector being configured to be inserted into the housing, at a position different from a position in the housing where the first connector is inserted, to discharge the cleaning solution, and configured to discharge the cleaning solution in a second direction in which the second connector is inserted into the housing; and a coupling part coupling the first holder and the second holder so that a first discharging direction along the first direction in which the cleaning solution is discharged from the first connector intersects a second discharging direction along the second direction in which the cleaning solution is discharged from the second connector.

According to another aspect of one or more embodiments, a cleaning tool is a cleaning tool for a surgical instrument that includes a housing. The cleaning tool includes: a first connector arranged at an end of a first tube configured to supply a cleaning solution for cleaning an inside of the housing, the first connector being configured to be inserted into a first port provided in the housing to discharge the cleaning solution in a first direction in which the first connector is inserted into the first port; a first holder holding the first connector; a second connector arranged at an end of a second tube configured to supply the cleaning solution, the second connector being configured to be inserted into a second port provided in the housing to discharge the cleaning solution in a second direction in which the second connector is inserted into the second port; a second holder holding the second connector; and a coupling part coupling the first holder and the second holder so that a first discharging direction along the first direction in which the cleaning solution is discharged from the first connector intersects a second discharging direction along the second direction in which the cleaning solution is discharged from the second connector.

According to various embodiments, the first discharging direction, which is an opposite direction to a direction in which a reaction force caused by discharge of the cleaning solution in the first connector acts, intersects the second discharging direction along the directions in which the second connector is inserted and pulled out. Thus, when the first connector receives a force in a direction to be pulled out of the housing due to the reaction force caused by the discharge of the cleaning solution, the second connector to which the first connector is coupled by the coupling part restricts movement of the first connector.

In some embodiments, the second discharging direction along an opposite direction to a reaction force caused by discharge of the cleaning solution in the second connector intersects the first discharging direction along the directions in which the first connector is inserted and pulled out. Thus, when the second connector receives a force in a direction to be pulled out of the housing due to the reaction force caused by the discharge of the cleaning solution, the first connector to which the second connector is coupled by the coupling part restricts movement of the second connector.

In some embodiments, a range of an intersecting angle between the first discharging direction and the second discharging direction may be from more than 45 degrees to 90 degrees or less.

In some embodiments, a reaction force caused by the discharge of the cleaning solution in the first connector may include a component in a parallel direction to the second discharging direction that is smaller than a component in a vertical direction to the second discharging direction. The component of the reaction force in the vertical direction is transmitted to the second connector and becomes a force to press the second connector against the housing in the vertical direction to the second discharging direction. A friction force to act between the second connector and the housing increases due to the component of the reaction force in the vertical direction to the second discharging direction. Since the component of the reaction force to act on the first connector in the parallel direction is relatively smaller, the movement of the first connector is restricted. Since the component of the reaction force to act in the vertical direction to the second discharging direction is relatively greater, the second connector is not easily pulled from the housing and restricts the movement of the first connector.

In some embodiments, the reaction force caused by the discharge of the cleaning solution in the second connector may include a component in a parallel direction to the first discharging direction that is smaller than a component in a vertical direction to the first discharging direction. The component of the reaction force in the vertical direction is transmitted to the first connector and becomes a force to press the first connector against the housing in the vertical direction to the first discharging direction. A friction force to act between the first connector and the housing increases due to the component of the reaction force in the vertical direction to the first discharging direction. Since the component of the reaction force to act on the second connector in the parallel direction to the first discharging direction is relatively smaller, the movement of the first connector is restricted. Since the component in the vertical direction to the first discharging direction is relatively greater, the first connector is not easily pulled from the housing and the first connector restricts the movement of the second connector.

In some embodiments, a range of an intersecting angle between the first discharging direction and the second discharging direction may be from more than 90 degrees to 180 degrees or less.

In some embodiments, the component of the reaction force caused by the discharge of the cleaning solution in the first connector in the parallel direction to the second discharging direction may act in an opposite direction to the direction in which the second connector is pulled out of the housing. Thus, the second connector restricts the movement of the first connector to a greater degree.

In some embodiments, the component of the reaction force caused by the discharge of the cleaning solution in the second connector in the parallel direction to the first discharging direction may act in an opposite direction to the direction in which the first connector is pulled out of the housing. Thus, the first connector restricts the movement of the second connector to a greater degree.

In some embodiments, the coupling part may have elasticity to cause the first holder and the second holder to be displaced in directions in which the first holder and the second holder approach and are separated from each other.

By having elasticity in the coupling part, the first holder and the second holder can be applied with a force to act in the direction in which they approach each other (in the direction in which they intend to approach each other). In other words, the force can be also understood as a force in a direction from the first holder to the second holder and/or a force in a direction from the second holder to the first holder. To put it differently, the first connector and the second connector can be applied with a force to act in a direction in which they approach each other (in a direction in which they intend to approach each other). Similarly, to put it in another way, the force can be also understood as a force in a direction from the first connector to the second connector and/or a force in a direction from the second connector to the first connector. At least a part of the force to act in an approaching direction by the coupling part becomes the force to press the first connector against the housing. Furthermore, at least a part of the force to act in the approaching direction by the coupling part becomes the force to press the second connector against the housing.

In some embodiments, the coupling part may be provided with an elastic part configured to be elastically deformed so that the first holder and the second holder are displaced in directions in which the first holder and the second holder approach and are separated.

By providing the coupling part with the elastic part, the coupling part does not require elasticity in the other part thereof, allowing for a broader range of choices in materials and shapes for forming the coupling part.

In some embodiments, the first connector may have a projecting shape whose outer surface is a circumferential surface; the first connector may be configured to be inserted into and pulled out of the first port having a recessed shape whose inner surface is a circumferential surface; the second connector may have a projecting shape whose outer surface is a circumferential surface; the second connector may be configured to be inserted into and pulled out of the second port having a recessed shape whose inner surface is a circumferential surface; and a first interference may be smaller than a second interference, the first interference being a value obtained by subtracting an inner circumference diameter, which is a diameter of the inner surface of the first port, from an outer circumference diameter, which is a diameter of the outer surface of the first port, and the second interference being a value obtained by subtracting an inner circumference diameter, which is a diameter of the inner surface of the second port, from an outer circumference diameter, which is a diameter of the outer surface of the second connector.

Since the first interference is smaller than the second interference, a force to insert the first connector into the first port is smaller than a required force to insert the second connector into the second port. Furthermore, a force to pull the first connector out of the first port is smaller than a force to pull the second connector out of the second port. In other words, a force to insert the second connector into the second port is greater than a force to insert the first connector into the first port. Furthermore, a force to pull the second connector out of the second port is greater than a force to pull the first connector out of the first port. Thus, a force of the second connector to restrict pulling out of the first connector due to the reaction force is greater than a force of the first connector to restrict pulling out of the second connector due to the reaction force.

By enabling the first connector to be easily inserted into and pulled out of the first port, attachment and removal of the cleaning tool can be facilitated. At the same time, during cleaning procedure, the second connector can restrict pulling out of the first connector from the first port due to the reaction force.

According to the cleaning tool of various embodiments, the second connector restricts the movement of the first connector in the direction in which the first connector is pulled from the housing; and the first connector restricts the movement of the second connector in the direction in which the second connector is pulled from the housing. Accordingly, the cleaning tool of various embodiments inhibit pulling out of the first connector and the second connector from the housing during cleaning while enabling stable cleaning of the inside of the surgical instrument (the inside of the housing).

With reference to FIGS. 1 to 12, a description is given to a cleaning tool 10 according to various embodiments. With reference to FIG. 1, the cleaning tool 10 is a tool to be used in cleaning a surgical instrument 50 for use in surgery (see also, FIGS. 7 and 8 for the cleaning tool 10). More specifically, the cleaning tool 10 is used when WD cleaning (WD: washer disinfector) is performed on the surgical instrument 50.

In an example, the surgical instrument 50 is mounted on a surgery assistance robot of the master-slave type (illustration omitted). The surgery assistance robot of the master-slave type is a surgery assistance robot whose specification allows a surgeon to operate a console (master) at hand to thereby control a manipulator (slave: corresponding to an arm and a hand of the robot) inserted into the body of the patient.

The cleaning tool 10 is a tool used when an inside of the surgical instrument 50 (an inside of a housing 51 of the surgical instrument 50) is cleaned by supplying a cleaning solution into the housing 51. The cleaning solution is supplied from a separate body 40 connected to the cleaning tool 10. The body 40 is a device to perform the WD cleaning. The cleaning tool 10 is a tool to be used to connect the body 40 and the surgical instrument 50.

Figure 2:
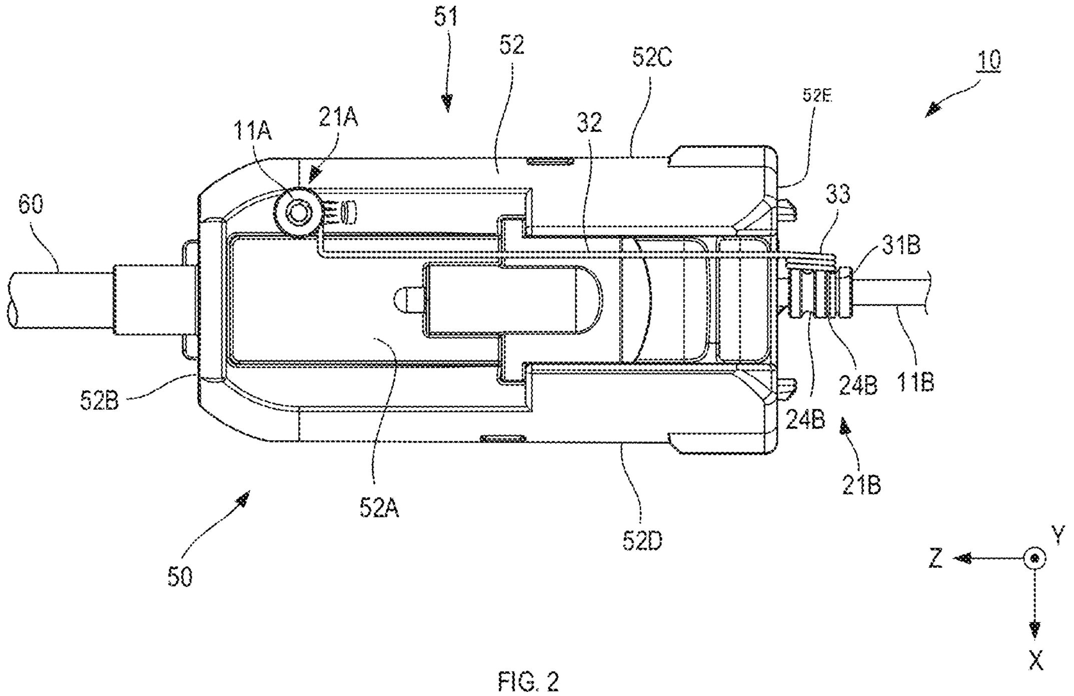
FIG. 2 is a top view explaining the configurations of the cleaning tool and the surgical instrument, according to some embodiments.

As illustrated in FIGS. 1 and 2, the cleaning tool 10 includes a first holder 31A, a second holder 31B, and a coupling part 32. In some embodiments, an elastic part 33 may be included. A first connector 21A and a second connector 21B are connected to the cleaning tool 10. A first tube 11A is coupled to the cleaning tool 10 via the first connector 21A, and a second tube 11B is coupled to the cleaning tool 10 via the second connector 21B.

The first tube 11A and the second tube 11B are tubular members to introduce the cleaning solution from the body 40 to the housing 51. In some embodiments, an end of the first tube 11A and an end of the second tube 11B adjacent to the body 40 may be detachably connected to the body 40. In some embodiments, the end of the first tube 11A and the end of the second tube 11B adjacent to the body 40 may be fixed to the body 40. The first tube 11A and the second tube 11B are formed by using a resin material with flexibility.

The first connector 21A and the second connector 21B are members arranged at an end of the first tube 11A adjacent to the housing 51 and an end of the second tube 11B adjacent to the housing 51, respectively. The first connector 21A is a part inserted into a first port 55A (FIGS. 4 and 5) of the housing 51. The second connector 21B is a part inserted into a second port 55B (see, FIGS. 4 and 6). The first connector 21A and the second connector 21B are configured to be pulled out of the housing 51 by applying a force in a direction opposite to respective insertion directions thereof. The first port 55A and the second port 55B of the housing 51 will be described later.

Figure 3:
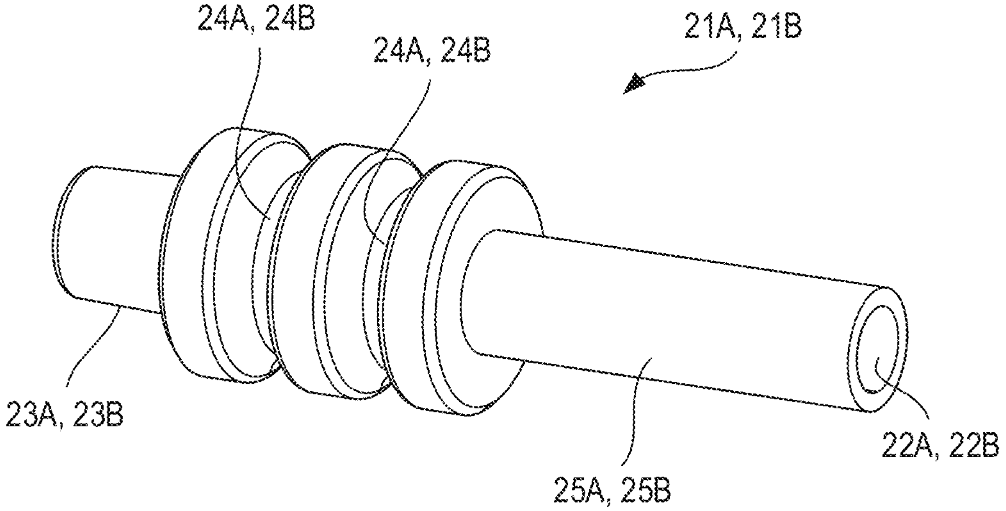
FIG. 3 is a perspective view explaining shapes of a first connector and a second connector, according to some embodiments.

The first connector 21A and the second connector 21B have the same shape. As illustrated in FIG. 3, the first connector 21A and the second connector 21B are formed into substantially circular cylindrical shapes, and include through-holes 22A and 22B, respectively, extending along center axes of the circular cylindrical shapes. The through-holes 22A and 22B are flow paths to carry the cleaning solution. The cleaning solution flows in extending directions of the through-holes 22A and 22B, in other words, in extending directions of the center axes of the circular cylindrical shapes. That is, the first connector 21A is configured in a manner such that a discharging direction of the cleaning solution into the housing 51 and the insertion direction of the first connector 21A into the first port 55A are the same. Similarly, the second connector 21B is configured in a manner such that a discharging direction of the cleaning solution into the housing 51 and the insertion direction of the second connector 21B into the second port 55B are the same.

The first connector 21A and the second connector 21B include parts, adjacent to the housing 51, that are provided with housing-side ends 23A and 23B. The housing-side ends 23A and 23B have circular truncated cone shapes whose diameters are decreased towards leading edges. Along central axes of the housing-side ends 23A and 23B, the through-holes 22A and 22B extend, respectively.

The first connector 21A and the second connector 21B each include a center part in a longitudinal direction that is formed to have a larger outer diameter as compared to parts on the both sides thereof. The center part in the longitudinal direction of the first connector 21A is provided with two grooves 24A and 24A on which the first holder 31A (see, FIGS. 1, 7, and 8) is disposed. The center part in the longitudinal direction of the second connector 21B is provided with two grooves 24B and 24B on which the second holder 31B (see, FIGS. 1, 7, and 8) is disposed.

In a part of the first connector 21A adjacent to the first tube 11A, there is provided a tube-side end 25A inserted into the first tube 11A. In a part of the second connector 21B adjacent to the second tube 11B, there is provided a tube-side end 25B inserted into the second tube 11B.

Figure 4:
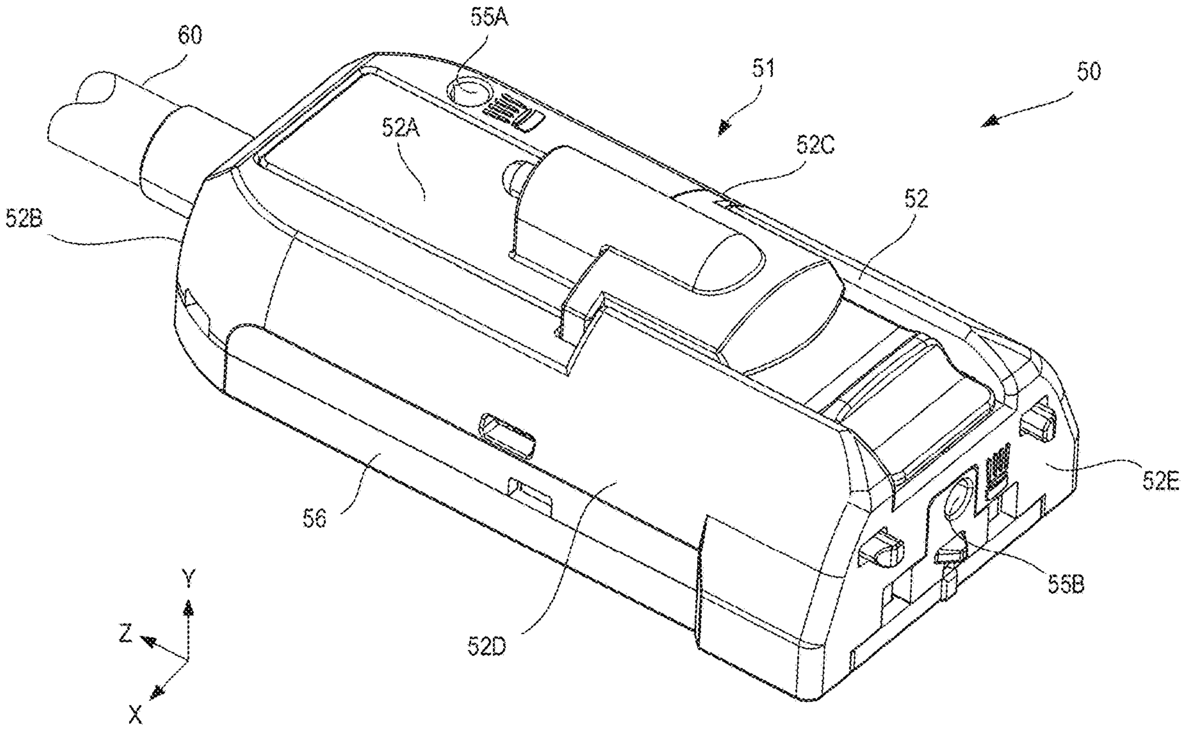
FIG. 4 is a perspective view explaining positions of a first port and a second port in the surgical instrument, according to some embodiments.

As illustrated in FIGS. 1 and 4, the surgical instrument 50 includes the housing 51 and a shaft 60. The housing 51 is a container including an internal space, and includes a cover 52 and a base 56 that comprises a mounting surface 57 to mount the surgical instrument 50 to, for example, a surgery assistance robot.

Hereinafter, a description is given by using an X-direction, a Y-direction, and a Z-direction to be described below. A direction parallel to the shaft 60 is the Z-direction. A positive direction of the Z-direction is a direction away from the housing 51. The X-direction and the Y-direction are directions extending along a plane orthogonal to the shaft 60, and are directions orthogonal to each other.

The X-direction is a direction extending along the mounting surface 57 in the base 56 of the housing 51. A positive direction of the X-direction is a left-obliquely downward direction in the paper of FIG. 4, and a downward direction in the paper of FIG. 2. The Y-direction is a direction orthogonal to the mounting surface 57, and a positive direction of the Y-direction is a direction from the base 56 to the cover 52 of the housing 51.

The cover 52 forms a contour of the housing 51 together with the base 56, and is a member forming the internal space of the housing 51. As illustrated in FIGS. 2 and 4, the cover 52 includes an upper surface 52A, a front surface 52B, side surfaces 52C and 52D, and a rear surface 52E.

The upper surface 52A is a surface that extends along a Z-X plane, and that is positioned on a positive side of the cover 52 in the Y-direction. The front surface 52B is a surface that extends along an X-Y plane, and that is positioned on a positive side of the cover 52 in the Z-direction. The side surfaces 52C and 52D are surfaces that extend along a Y-Z plane, and that are positioned on a negative side and a positive side of the cover 52 in the X-direction. The rear surface 52E is a surface that extends along the X-Y plane, and that is positioned on a negative side of the cover 52 in the Z-direction.

The cover 52 is provided with the first port 55A. Hereinafter, the first port 55A is also referred to as “flush port”. The upper surface 52A of the cover 52 is provided with the first port 55A. The first port 55A may be provided in the front surface 52B of the cover 52, or the side surface 52C or the side surface 52D of the cover 52.

The first port 55A is a through-hole that penetrates the cover 52 and extends in the Y-direction. Specifically, the first port 55A is a through-hole penetrating the upper surface 52A. The first port 55A is a through-hole used when the cleaning solution is supplied into the internal space of the housing 51 from the outside of the housing 51.

Figure 5:
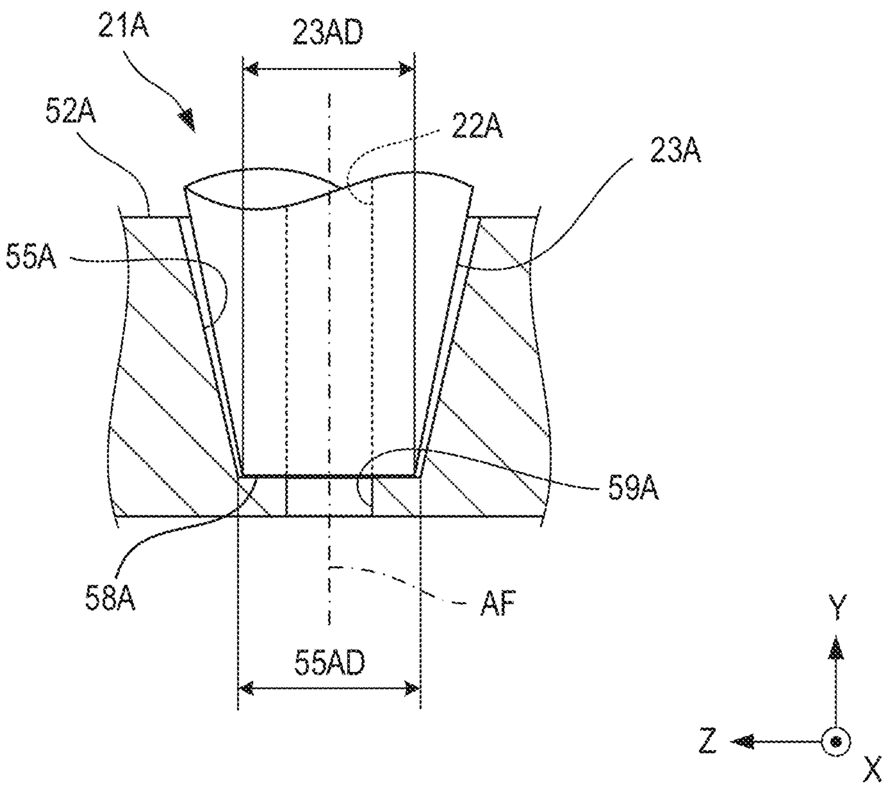
FIG. 5 is a schematic diagram explaining a first interference between the first connector and the first port, according to some embodiments.

As illustrated in FIG. 5, a side surface of a part of the first port 55A in which the first connector 21A is inserted tilts at an angle corresponding to the circular truncated cone shape of the housing-side end 23A. Specifically, the side surface of the part of the first port 55A in which the housing-side end 23A is inserted includes a conical surface whose diameter increases towards the outside of the housing 51. A side of the first port 55A at the inside of the housing 51 is provided with a bottom 58A, which is provided with a hole 59A to carry the cleaning solution.

An inner circumference diameter 55AD, which is a diameter of the bottom part of the first port 55A, is equal to or greater than an outer circumference diameter 23AD, which is a diameter of the leading edge of the housing-side end 23A of the first connector 21A. In the description hereinafter given, a value obtained by subtracting the inner circumference diameter 55AD of the bottom part from the outer circumference diameter 23AD of the leading edge is referred to as “first interference AC”. As illustrated in FIG. 5, when the first connector 21A is inserted into the first port 55A, the leading edge of the first connector 21A contacts the bottom 58A of the first port 55A.

The base 56 is a plate-shaped member that forms the contour of the housing 51 together with the cover 52, and forms a part to be attached to the surgery assistance robot. As illustrated in FIGS. 1 and 4, the cover 52 is arranged on a positive side of the base 56 in the Y-direction. A surface on a negative side of the base 56 in the Y-direction is the mounting surface 57. The mounting surface 57 is a surface to mount the surgical instrument 50 on the surgery assistance robot, and to contact the surgery assistance robot.

At an end on a positive side of the base 56 in the Z-direction, the shaft 60 is attached. At an end on a negative side of the base 56 in the Z-direction, there is provided the second port 55B. Hereinafter, the second port 55B is also referred to as “main flush port”. The second port 55B (main flush port) is a through-hole used when the cleaning solution is supplied into the shaft 60 from the outside of the housing 51.

The second port 55B is provided to a part of the base 56 extending towards the cover 52 (the positive side in the Y-direction). In other words, the second port 55B is provided to the part of the base 56 extending towards the positive side in the Y-direction at an end on the negative side in the Z-direction. The second port 55B is a through-hole extending in the Z-direction.

Figure 6:
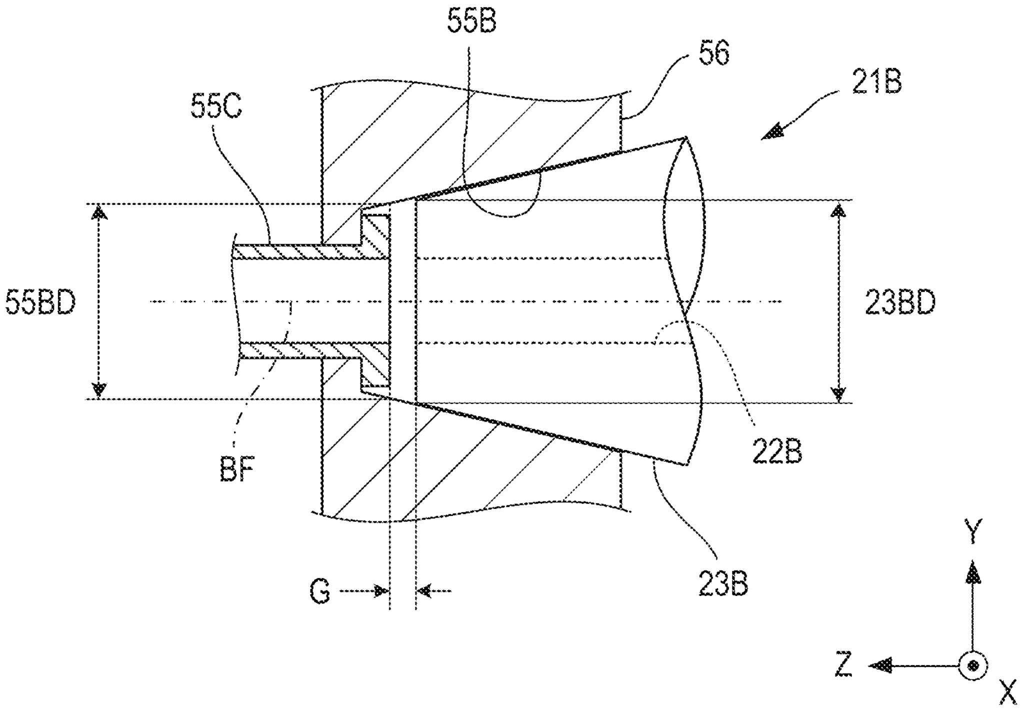
FIG. 6 is a schematic diagram explaining a second interference between the second connector and the second port, according to some embodiments.

As illustrated in FIG. 6, a side surface of a part of the second port 55B in which the second connector 21B is inserted tilts at an angle corresponding to the circular truncated cone shape of the housing-side end 23B. Specifically, the side surface of the part of the second port 55B in which the housing-side end 23B is inserted includes a conical surface whose diameter increases towards the outside of the housing 51. The second port 55B is, at the inside of the housing 51, is provided with a flush tube 55C. The flush tube 55C is a tubular member to guide the cleaning solution supplied via the second port 55B to a specific part. Hereinafter, the side surface of the first port 55A on a side where the housing-side end 23A is inserted and the side surface of the second port 55B on a side where the housing-side end 23B is inserted are also referred to as “inner circumferential surfaces”. Furthermore, a side surface of the housing-side end 23A on a side inserted into the first port 55A and a side surface of the housing-side end 23B on a side inserted into the second port 55B are also referred to as “outer circumferential surfaces”.

An inner circumference diameter 55BD, which is a diameter of the second port 55B at a position of an end face of the flush tube 55C, is smaller than an outer circumference diameter 23BD, which is a diameter of the leading edge of the housing-side end 23B of the second connector 21B. In the description hereinafter given, a value obtained by subtracting the inner circumference diameter 55BD at the position of the end face from the outer circumference diameter 23BD of the leading edge is referred to as “second interference BC”. As illustrated in FIG. 6, when the second connector 21B is inserted into the second port 55B, the leading edge of the second connector 21B stops at a position away from the end face of the flush tube 55C.

In the above description, the first interference AC is a negative value, and the second interference BC is a positive value. In other words, the first interference AC is smaller than the second interference BC. A fit between the first connector 21A and the first port 55A is also referred to as “clearance fit”. Furthermore, a fit between the second connector 21B and the second port 55B is referred to as “interference fit”. It should be noted that although the description has been given hereinabove by showing an example case where the fit between the first connector 21A and the first port 55A is the clearance fit, the fit between the first connector 21A and the first port 55A can be the interference fit in any case in which the first interference AC is smaller than the second interference BC. That is, the inner circumference diameter 55AD can be smaller than the outer circumference diameter 23AD to the extent that the first interference AC is smaller than second interference BC. That is, the fit between the first connector 21A and the first port 55A can be the interference fit if the first connector 21A can be easily inserted into and pulled out of the first port 55A as compared with a case where the second connector 21B is inserted into and pulled out of the second port 55B.

As illustrated in FIG. 1, the first holder 31A is a member configured to hold the first connector 21A. Specifically, the first holder 31A is a member that is configured to be engaged with one of the grooves 24A and 24A in FIG. 3 and to hold the first connector 21A.

Figure 7:
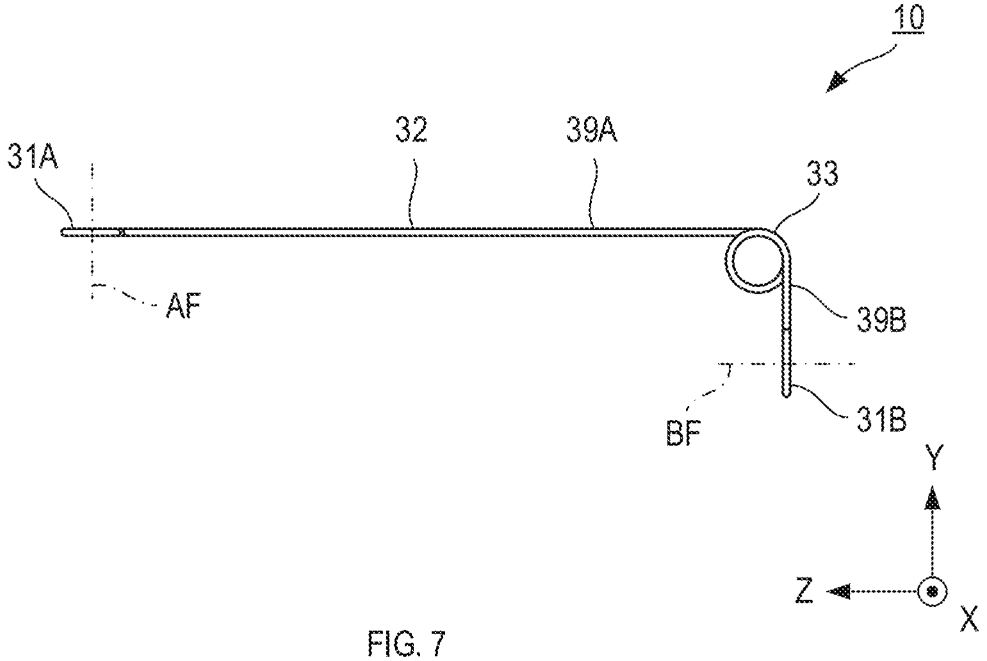
FIG. 7 is a front view explaining the configuration of the cleaning tool, according to some embodiments.
Figure 8:
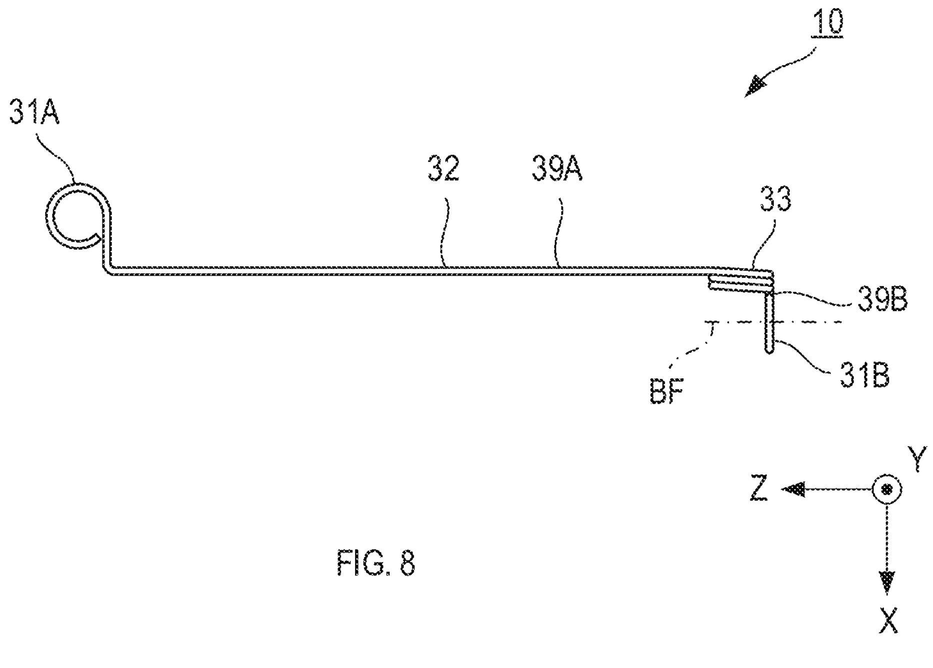
FIG. 8 is a top view explaining the configuration of the cleaning tool, according to some embodiments.

As illustrated in FIGS. 7 and 8, the first holder 31A is provided to an end on a positive side in a Z-axis of the coupling part 32. The first holder 31A has an arc-like shape extending along the groove 24A. As illustrated in FIG. 8, the first holder 31A has an arc-like shape arranged on the Z-X plane.

It should be noted that the first holder 31A can have any shape that can hold the first connector 21A, and may have a shape different from the arc-like shape. Furthermore, the first holder 31A may have a shape that allows the first connector 21A to be detachably attached with ease.

As illustrated in FIGS. 1 and 2, the second holder 31B is a member to hold the second connector 21B. Specifically, the second holder 31B is a member to be arranged on one of the grooves 24B and 24B in FIG. 3, and to hold the second connector 21B.

As illustrated in FIGS. 7 and 8, the second holder 31B is provided to an end on a negative side in the Z-axis of the coupling part 32, which is an end on a negative side in a Y-axis. In the present embodiment, the second holder 31B has an arc-like shape extending along the groove 24B. As illustrated in FIG. 7, the second holder 31B has an arc-like shape arranged on the X-Y plane.

It should be noted that the second holder 31B can have any shape that can hold the second connector 21B, and may have a shape different from the arc-like shape. Furthermore, the second holder 31B may have a shape that allows the second connector 21B to be detachably attached with ease.

As illustrated in FIGS. 7 and 8, the coupling part 32 is a part formed into a line (e.g., a wire, rod, bar, etc.) that connects the first holder 31A and the second holder 31B. As illustrated in FIG. 7, the coupling part 32 includes a first portion 39A that linearly extends along the Z-axis, and a second portion 39B that linearly extends along the Y-axis towards the negative side. As illustrated in FIG. 7, the elastic part 33 is provided between the first portion 39A and the second portion 39B. In other words, the elastic part 33 is provided at a position where the coupling part 32 is bent.

As illustrated in FIG. 8, the first holder 31A is provided at an end of the first portion 39A. Furthermore, the second holder 31B is provided at an end of the second portion 39B.

The center axis of the first holder 31A formed into the arc-like shape extends in parallel to a first discharging direction AF, which is a direction to discharge the cleaning solution into the housing 51 from the first connector 21A held by the first holder 31A. The center axis of the second holder 31B formed into the arc-like shape extends in parallel to a second discharging direction BF, which is a direction to discharge the cleaning solution into the housing 51 from the second connector 21B held by the second holder 31B.

The first discharging direction AF and the second discharging direction BF intersect at an angle of 90 degrees. The intersecting angle between the first discharging direction AF and the second discharging direction BF may be an angle in a range from more than 45 degrees to 90 degrees or less. Furthermore, the intersecting angle between the first discharging direction AF and the second discharging direction BF may be an angle in a range from more than 90 degrees to 180 degrees or less. The intersecting angle means an angle formed by the first discharging direction AF and the second discharging direction BF. The intersecting angle covers a case where the angle formed by the first discharging direction AF and the second discharging direction BF is 180 degrees.

The elastic part 33 is a member made by forming a linear member (e.g., a wire, rod, bar, etc.) into a helical shape. The elastic part 33 is a member that is formed by winding a linear member (e.g., a wire, rod, bar, etc.) forming the coupling part 32 in the helical form. That is, the linear members forming the elastic part 33 and the coupling part 32 are continuous. In some embodiments, the elastic part 33 may be a spring, such as a coil spring, a leaf spring, etc.

Figure 9:
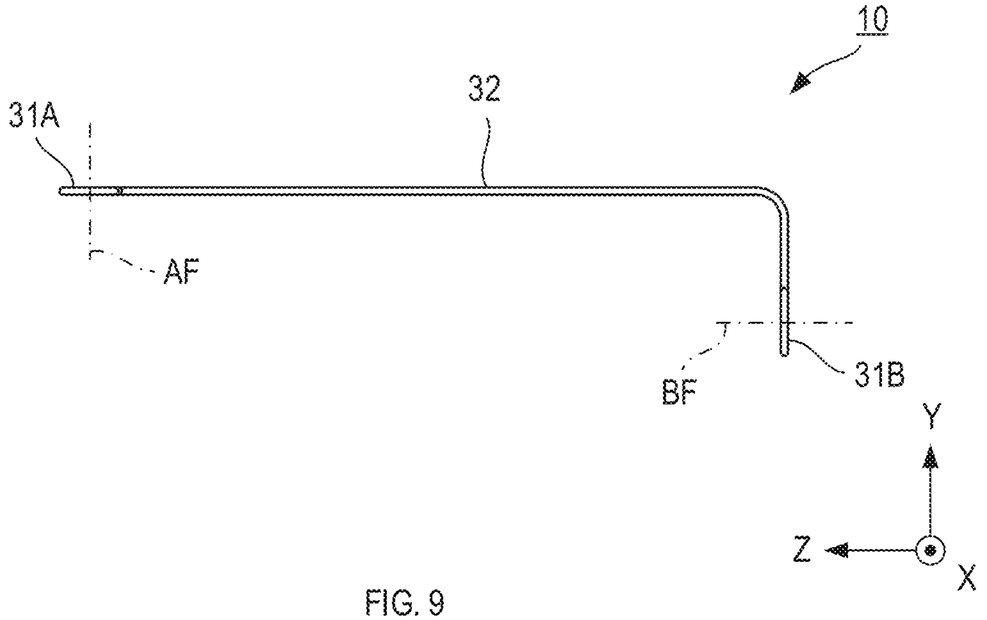
FIG. 9 is a front view explaining a cleaning tool, according to some embodiments.

It should be noted that a configuration in which the elastic part 33 as illustrated in FIGS. 7 and 8 is omitted can be achieved by bending an elastic linear member (e.g., a wire, a bar, a rod, etc.) as illustrated in FIG. 9 to thereby form the coupling part 32. Furthermore, a non-elastic linear member may be bent to form the coupling part 32 in any circumstance that enables the first holder 31A and the second holder 31B to be property coupled in accordance with the various embodiments.

Figure 10:
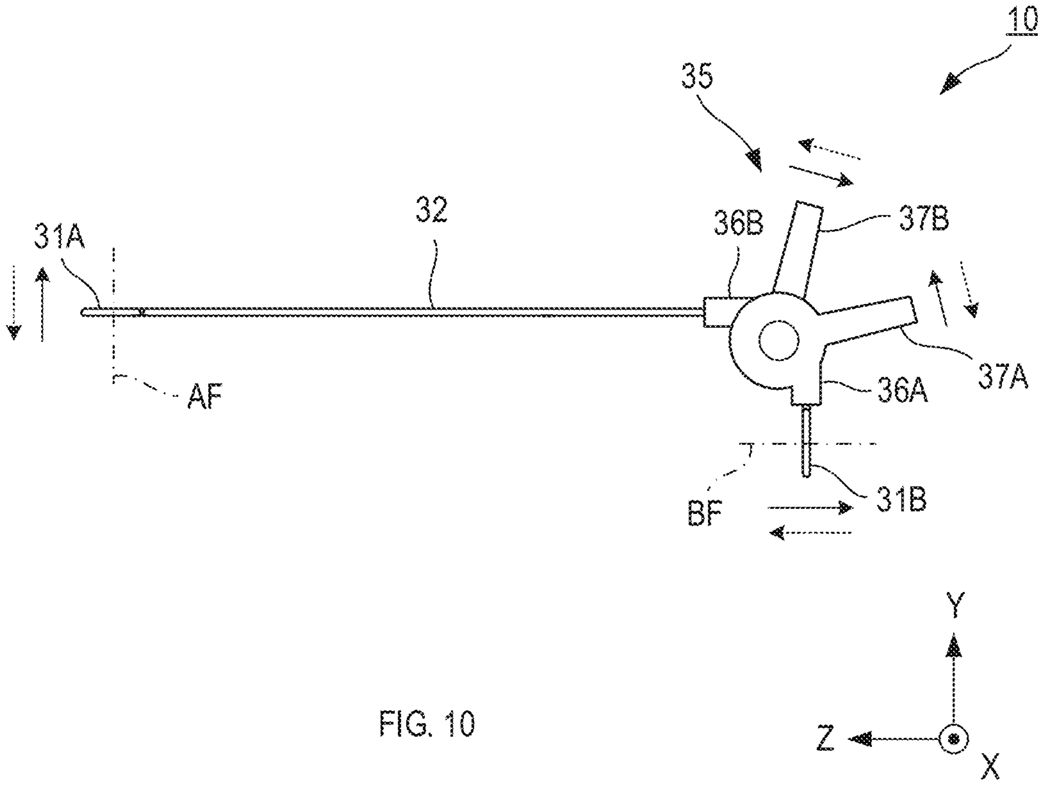
FIG. 10 is a front view explaining a cleaning tool, according to some embodiments.

Furthermore, as illustrated in FIG. 10, in some embodiments, the elastic part 33 may be covered by a clamp 35. The clamp 35 comprises two rotating parts 36A and 36B that are rotatable to each other, and opening and closing parts 37A and 37B that have a rod-shape extending from the two rotating parts 36A and 36B.

When the opening and closing parts 37A and 37B are made to approach each other, the rotating parts 36A and 36B pivot, respectively. The pivot movement of the rotating parts 36A and 36B is transmitted to the coupling part 32, and the first holder 31A and the second holder 31B move in respective separating directions. Furthermore, when the opening and closing parts 37A and 37B are made to be spaced apart, the rotating parts 36A and 36B pivot towards respective sides opposite to the aforementioned. The pivot movement of the two rotating parts 36A and 36B is transmitted to the coupling part 32, and the first holder 31A and the second holder 31B move in respective approaching directions.

Next, a description is given to cleaning of the surgical instrument 50 utilizing the cleaning tool 10 according to the above-described embodiments. In the case of cleaning the surgical instrument 50, as illustrated in FIG. 1, the cleaning tool 10 is attached to the surgical instrument 50. For example, the first connector 21A and the second connector 21B are inserted into the flush port (the first port 55A) and the main flush port (the second port 55B) (see, FIG. 4) of the surgical instrument 50, respectively.

As illustrated in FIG. 5, the first connector 21A is inserted into the first port 55A along the Y-direction. Since the first connector 21A and the first port 55A are placed in the clearance fit, the housing-side end 23A of the first connector 21A is inserted until the leading edge thereof contacts the bottom of the first port 55A. There remains a gap between the outer circumferential surface of the housing-side end 23A and the inner circumferential surface of the first port 55A.

As illustrated in FIG. 6, the second connector 21B is inserted into the second port 55B along the Z-direction. Since the second connector 21B and the second port 55B are placed in the interference fit, the housing-side end 23B of the second connector 21B is inserted until the outer circumferential surface thereof contacts the inner circumferential surface of the second port 55B. There remains a gap G between the leading edge of the housing-side end 23B and the end face of the flush tube 55C in the second port 55B.

When the cleaning tool 10 is attached to the surgical instrument 50, the cleaning solution is supplied from the main body 40. The flow rate, the component, the temperature, and the like of the cleaning solution supplied from the main body 40 may be controlled over time in accordance with a specific pattern.

The cleaning solution is supplied into the housing 51 of the surgical instrument 50 via the cleaning tool 10. The inside of the housing 51 is cleaned by the cleaning solution that is supplied into the housing 51. The cleaning solution that has cleaned the inside of the housing 51 is released to the outside through a gap in the housing 51.

Figure 11:
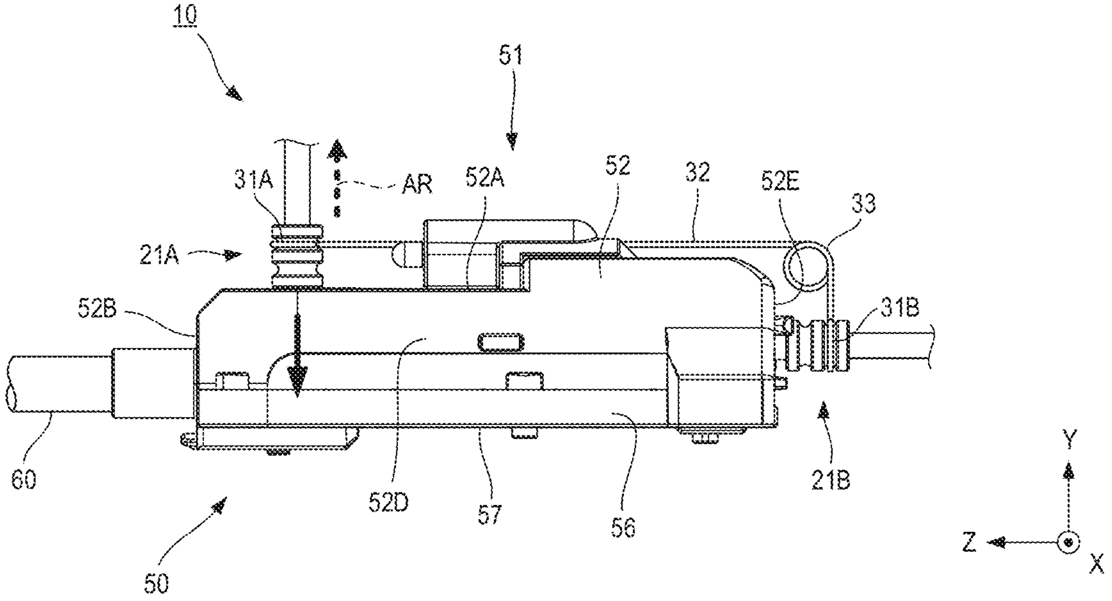
FIG. 11 is a front view explaining a force to act on the first connector, according to some embodiments.

The cleaning solution supplied from the main body 40 is, as indicated by the solid line arrow in FIG. 11, injected into the housing 51 from the first connector 21A towards the negative side in the Y-direction via the first tube 11A. Upon injection of the cleaning solution into the housing 51, a reaction force AR against the injection of the cleaning solution acts on the first connector 21A towards the positive side in the Y-direction, as indicated by the dotted line arrow.

The first holder 31A is formed integrally with the coupling part 32 and the second holder 31B, and the second holder 31B holds the second connector 21B. The second connector 21B is inserted into the second port 55B in the Z-direction, that is, in a direction forming an angle of 90 degrees with respect to the direction of the reaction force AR. The reaction force AR is received by the second connector 21B inserted into the second port 55B through the coupling part 32. Thus, the first connector 21A is kept inserted in the first port 55A without being pulled therefrom due to the reaction force AR.

Figure 12:
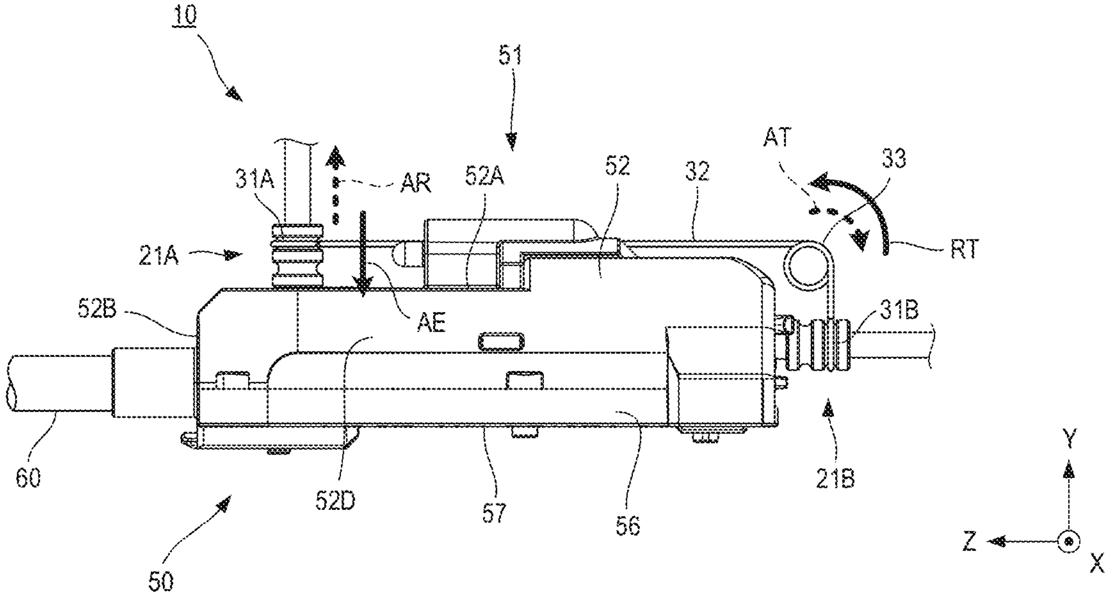
FIG. 12 is a front view explaining a force to act by an elastic part, according to some embodiments.

As illustrated in FIG. 12, the reaction force AR causes a torsion torque AT to be applied on the elastic part 33. The elastic part 33 is elastically deformed upon receipt of the torsion torque AT, and the elastic deformation generates a torsion torque RT in an opposite direction to the torsion torque AT.

Due to the torsion torque RT, a force AE in an opposite direction to the reaction force AR is applied to the first holder 31A. The force AE is a force in a direction to make the first holder 31A and the second holder 31B approach each other, that is, a force in a direction to press the first holder 31A against the housing 51.

The reaction force caused by the injection of the cleaning solution also acts on the second connector 21B. As in the case of the first connector 21A, the reaction force acting on the second connector 21B is received by the first connector 21A inserted into the first port 55A. Thus, the second connector 21B is kept inserted in the second port 55B. Furthermore, since the outer circumferential surface of the housing-side end 23B contacts the inner circumferential surface of the second port 55B, a fiction force acts between the housing-side end 23B and the second port 55B. The second connector 21B is also kept inserted in the second port 55B by the friction force.

According to the cleaning tool 10 of as described above, the first discharging direction AF, which is an opposite direction to a direction in which a reaction force acts due to discharge of the cleaning solution in the first connector 21A intersects the second discharging direction BF, which is an opposite direction to a direction in which a reaction force acts due to discharge of the cleaning solution in the second connector 21B. That is, the direction in which the reaction force acts due to the discharge of the cleaning solution in the first connector 21A intersects the direction in which the second connector 21B is inserted and pulled out. Thus, when the first connector 21A is moved in the direction to be pulled out of the first port 55A due to the reaction force caused by the discharge of the cleaning solution, the movement of the first connector 21A is restricted by the second connector 21B to which the first connector 21A is coupled by the coupling part 32. That is, the first connector 21A is not easily pulled from the first port 55A even when the reaction force acts due to the discharge of the cleaning solution.

Furthermore, the second discharging direction BF, which is an opposite direction to a direction in which a reaction force acts due to the discharge of the cleaning solution in the second connector 21B, intersects the first discharging direction AF, which is an opposite direction to a direction in which a reaction force acts due to the discharge of the cleaning solution in the first connector 21A. That is, the direction in which the reaction force acts due to the discharge of the cleaning solution in the second connector 21B intersects the direction in which the first connector 21A is inserted and pulled out. Thus, when the second connector 21B is moved in the direction to be pulled out of the second port 55B due to the reaction force, the movement is restricted by the first connector 21A to which the second connector 21B is coupled by the coupling part 32. That is, the second connector 21B is not easily pulled from the second port 55B even when the reaction force acts due to the discharge of the cleaning solution.

Since the elastic part 33 provided to the coupling part 32 has elasticity, the first holder 31A and the second holder 31B are applied with a force to act in directions in which the first holder 31A and the second holder 31B approach each other and are forced towards the housing 51. In other words, the first connector 21A and the second connector 21B are applied with a force to act in respective directions in which the first holder 31A and the second holder 31B approach each other. At least a part of the force to act in the approaching directions is the force to press the first connector 21A against the housing 51. Furthermore, at least a part of the force to act in the approaching directions is the force to press the second connector 21B against the housing 51. That is, the first connector 21A and the second connector 21B are not easily pulled from the first port 55A and the second port 55B.

The coupling part 32 does not require elasticity since the coupling part 32 is provided with the elastic part 33, allowing for a broader range of choices in materials and shapes for forming the coupling part 32.

Since the first interference AC is smaller than the second interference BC, a force to insert the first connector 21A into the first port 55A is smaller than a force to insert the second connector 21B into the second port 55B. In other words, due to the friction force between the outer circumferential surface of the housing-side end 23B and the inner circumferential surface of the second port 55B, a greater force is used when the second connector 21B is inserted into the second port 55B with respect to the force used when the first connector 21A is inserted into the first port 55A. Furthermore, when the second connector 21B is pulled out of the second port 55B, a greater force is used than when the first connector 21A is pulled out of the first port 55A. That is, in comparison with a case where the second connector 21B is inserted into and pulled out of the second port 55B, the first connector 21A can be easily inserted into and pulled out of the first port 55A. Moreover, upon insertion of the second connector 21B into the second port 55B, the resulting friction force causes the second connector 21B to be fixed to the second port 55B. Thus, a force of the second connector 21B to restrict pulling out of the first connector 21A due to the reaction force is greater than a force of the first connector 21A to restrict pulling out of the second connector 21B due to the reaction force.

By making the first connector 21A to be easily inserted into and pulled out of the first port 55A, the cleaning tool 10 is easily attached and removed. At the same time, during the cleaning procedure, the second connector 21B can restrict the pulling out of the first connector 21A from the first port 55A due to the reaction force.

If the intersecting angle between the first discharging direction AF and the second discharging direction BF is an angle in a range from more than 45 degrees to 90 degrees or less, the reaction force caused by the discharge of the cleaning solution in the first connector 21A has a component in a parallel direction to the second discharging direction BF that is smaller than a component in a vertical direction.

The component of the reaction force in the vertical direction is transmitted to the second connector 21B and becomes the force to press the second connector 21B against the second port 55B. The friction force acting between the second connector 21B and the second port 55B increases due to the component of the reaction force in the vertical direction.

Since the component of the reaction force to act on the first connector 21A in the parallel direction is relatively smaller, the movement of the first connector 21A is restricted. Since the component in the vertical direction is relatively greater, the second connector 21B is not easily pulled from the second port 55B and restricts the movement of the first connector 21A.

Furthermore, the reaction force caused by the discharge of the cleaning solution in the second connector 21B has a component in a parallel direction to the first discharging direction AF that is smaller than a component in a vertical direction. Since the component of the reaction force to act on the second connector 21B in the parallel direction is relatively smaller, the movement of the first connector 21A is restricted. Since the component in the vertical direction is relatively greater, the first connector 21A is not easily pulled from the first port 55A and the first connector 21A restricts the movement of the second connector 21B.

If the intersecting angle between the first discharging direction AF and the second discharging direction BF is an angle in a range from more than 90 degrees to 180 degrees or less, the component of the reaction force caused by the discharge of the cleaning solution in the first connector 21A in the parallel direction to the second discharging direction BF acts in an opposite direction to the direction in which the second connector 21B is pulled from the second port 55B. Thus, the second connector 21B restricts the movement of the first connector 21A to a greater degree.

Furthermore, the component of the reaction force caused by the discharge of the cleaning solution in the second connector 21B in the parallel direction to the first discharging direction AF acts in an opposite direction to the direction in which the first connector 21A is pulled from the first port 55A. Thus, the first connector 21A restricts the movement of the second connector 21B to a greater degree.

In the embodiments described with respect to FIGS. 1-12, the first connector 21A and the second connector 21B have a configuration that is independent of and separated from the cleaning tool 10, rather than being part of the cleaning tool 10. However, embodiments are not limited hereto.

In some embodiments, the cleaning tool 10 may comprise the first connector 21A and the second connector 21B. That is, in some embodiments, the first connector 21A and the second connector 21B may be included in the cleaning tool 10.

In embodiments described with respect to FIGS. 1-12, the first tube 11A and the second tube 11B have been described on the premise that they have a configuration that is independent of and separated from the cleaning tool 10, rather than being part of the cleaning tool 10. However, embodiments are not limited hereto. For example, in some embodiments, the cleaning tool 10 may comprise the first tube 11A and the second tube 11B. That is, the first tube 11A and the second tube 11B may be included in the cleaning tool 10.

Two or more functions of one element in the above-described embodiments may be distributed to two or more elements, and two or more functions of two or more elements may be integrated into one element. Furthermore, a part of the configurations in the above-described embodiments may be omitted. Still further, at least a part of the configurations in the above-described embodiments may be added to or replaced with a configuration in another one of the above-described embodiments.

While various embodiments have been particularly shown and described with reference to the drawings, it will be understood that various changes in form and details may be made therein without departing from the spirit and scope of the following claims.

The invention claimed is:

1. A cleaning tool for a surgical instrument that includes a housing, the cleaning tool comprising:

a first holder configured to hold a first connector, the first connector being configured to be inserted into the housing to discharge a cleaning solution in a first discharging direction for cleaning an inside of the housing, and the first discharging direction being parallel to a direction in which the first connector is inserted into the housing;

a second holder configured to hold a second connector, the second connector being configured to be inserted into the housing, at a position different from a position in the housing at which the first connector is inserted, to discharge the cleaning solution in a second discharging direction, and the second discharging direction being parallel to a direction in which the second connector is inserted into the housing; and a coupling part coupling the first holder and the second holder so that the first discharging direction intersects the second discharging direction.

2. The cleaning tool according to claim 1, wherein an intersecting angle between the first discharging direction and the second discharging direction is from 45 degrees to 90 degrees.

3. The cleaning tool according to claim 1, wherein an intersecting angle between the first discharging direction and the second discharging direction is from 90 degrees to 180 degrees.

4. The cleaning tool according to claim 1, wherein the coupling part has elasticity such that when the first holder is displaced away from the housing, the second holder is pressed into the housing, and when the second holder is displaced away from the housing, the first holder is pressed into the housing.

5. The cleaning tool according to claim 1, wherein the coupling part comprises an elastic part configured to be elastically deformed so that when the first holder is displaced away from the housing, the second holder is pressed into the housing, and when the second holder is displaced away from the housing, the first holder is pressed into the housing.

6. A cleaning tool for a surgical instrument that includes a housing, the cleaning tool comprising:

a first connector arranged at an end of a first tube configured to supply a cleaning solution for cleaning an inside of the housing, the first connector being configured to be inserted into a first port provided in the housing to discharge the cleaning solution in a first discharging direction parallel to a direction in which the first connector is inserted into the first port;

a first holder holding the first connector;

a second connector arranged at an end of a second tube configured to supply the cleaning solution, the second connector being configured to be inserted into a second port provided in the housing to discharge the cleaning solution in a second discharging direction parallel to a direction in which the second connector is inserted into the second port;

a second holder holding the second connector; and a coupling part coupling the first holder and the second holder so that the first discharging direction intersects the second discharging direction.

7. The cleaning tool according to claim 6, wherein the first connector has an outer circumferential surface, wherein the first port has a recessed shape with an inner circumferential surface, and the first connector is configured to be inserted into and pulled out of the first port, wherein the second connector has an outer circumferential surface, wherein the second port has a recessed shape with an inner circumferential surface, and the second connector is configured to be inserted into and pulled out of the second port, wherein a first interference is a value obtained by subtracting an inner circumference diameter of the inner circumferential surface of the first port from an outer circumference diameter of the outer circumferential surface of the first connector, wherein a second interference is a value obtained by subtracting an inner circumference diameter of the inner circumferential surface of the second port from an outer circumference diameter of the outer circumferential surface of the second connector, and wherein the first interference is smaller than the second interference.

8. The cleaning tool according to claim 6, wherein an intersecting angle between the first discharging direction and the second discharging direction is from 45 degrees to 90 degrees.

9. The cleaning tool according to claim 6, wherein an intersecting angle between the first discharging direction and the second discharging direction is from 90 degrees to 180 degrees.

10. The cleaning tool according to claim 6, wherein the coupling part has elasticity such that when the first holder is displaced to separate from the housing, the second holder is displaced to press into the housing, and when the second holder is displaced to separate from the housing, the first holder is displaced to press into the housing.

11. The cleaning tool according to claim 6, wherein the coupling part comprises an elastic part configured to be elastically deformed so that when the first holder is displaced to separate from the housing, the second holder is displaced to press into the housing, and when the second holder is displaced to separate from the housing, the first holder is displaced to press into the housing.

12. A cleaning tool comprising:

a first holder configured to engage a groove of a first connector at a distal end of a first tube, the first connector being removably received into a first port in a housing of a surgical instrument and being configured discharge a cleaning solution into the housing in a first discharging direction parallel to a direction in which the first connector is received into the first port;

a second holder configured to engage a groove of a second connector at a distal end of a second tube, the second connector being removably received into a second port in the housing and being configured to discharge the cleaning solution into the housing in a second discharging direction that is parallel to a direction in which the second connector is received into the second port and that intersects the first discharging direction; and a coupling rod coupling the first holder and the second holder.

13. The cleaning tool of claim 12, wherein the first port and the second port are in different walls of the housing.

14. The cleaning tool of claim 12, wherein the first port is in an upper surface of the housing and the second port is in a rear surface of the housing that is orthogonal to the upper surface of the housing.

15. The cleaning tool according to claim 12, wherein an intersecting angle between the first discharging direction and the second discharging direction is from 45 degrees to 90 degrees.

16. The cleaning tool according to claim 12, wherein an intersecting angle between the first discharging direction and the second discharging direction is from 90 degrees to 180 degrees.

17. The cleaning tool according to claim 12, wherein the coupling rod has elasticity such that when the first holder is displaced away from the housing, the second holder is pressed into the housing, and when the second holder is displaced away from the housing, the first holder is pressed into the housing.

18. The cleaning tool according to claim 12, wherein the coupling rod comprises an elastic spring between the first holder and the second holder, such that when first holder is displaced away from the housing, the second holder is pressed into the housing, and when the second holder is displaced away from the housing, the first holder is pressed into the housing.

19. The cleaning tool according to claim 12, wherein the cleaning tool further comprises the first connector and the second connector.

* * * * *